(12) United States Patent
Walter et al.

(10) Patent No.: US 7,678,924 B2
(45) Date of Patent: Mar. 16, 2010

(54) PROCESS FOR THE PREPARATION OF PYRAZOLES

(75) Inventors: Harald Walter, Basel (CH); Camilla Corsi, Basel (CH); Josef Ehrenfreund, Basel (CH); Clemens Lamberth, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 241 days.

(21) Appl. No.: 11/577,511

(22) PCT Filed: Oct. 19, 2005

(86) PCT No.: PCT/EP2005/011232

§ 371 (c)(1), (2), (4) Date: Apr. 19, 2007

(87) PCT Pub. No.: WO2006/045504

PCT Pub. Date: May 4, 2006

(65) Prior Publication Data

US 2009/0069572 A1    Mar. 12, 2009

(30) Foreign Application Priority Data

Oct. 21, 2004  (CH) ................................. 1750/04

(51) Int. Cl.
C07D 231/10 (2006.01)
(52) U.S. Cl. .................................... 548/374.1
(58) Field of Classification Search ............. 548/356.1, 548/373.1, 374.1
See application file for complete search history.

(56) References Cited

U.S. PATENT DOCUMENTS 5,523,280 A    6/1996  Chene et al.

FOREIGN PATENT DOCUMENTS

JP    2000044541 A    2/2000
WO    95/25099 A    9/1995

OTHER PUBLICATIONS

Paquette, L.A. (Ed.): "Encyclopedia of Reagents for Organic Synthesis, vol. 7" 1995, John Wiley & Sons, Chichester, XP002368410, pp. 5216-5217: Trimethyl Phosphate.

Yamauchi, K. et al.: "Esters of Phosphorus Oxy-acids as Alkylating Agents, Part II." J. Chem. Soc., Perkin Trans. 1, vol. 21, 1973, pp. 2506-2508, XP009062138.

*Primary Examiner*—Kamal A Saeed
*Assistant Examiner*—Samantha L Shterengarts
(74) *Attorney, Agent, or Firm*—William F. Mulholland, II

(57) ABSTRACT

The present invention relates to a process for the preparation of compounds of formula I

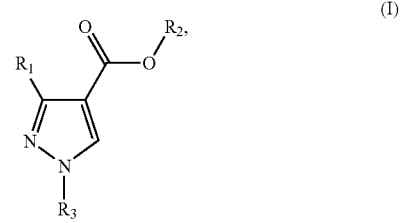

wherein $R_1$ is $C_1$-$C_4$haloalkyl; $R_2$ is $C_1$-$C_6$alkyl and $R_3$ is methyl or ethyl,
by reaction of compounds of formula II

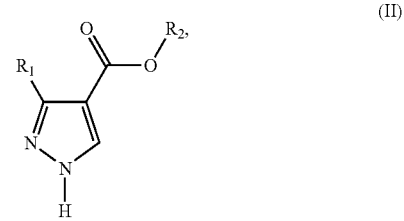

wherein the substituents are as defined for formula I, with compounds of formula III

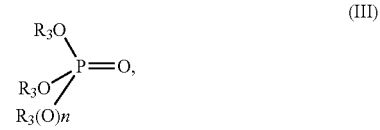

wherein $R_3$ is as defined for formula I and n is 0 or 1.

3 Claims, No Drawings

PROCESS FOR THE PREPARATION OF PYRAZOLES

This application is a 371 of International Application No. PCT/EP2005/011232 filed Oct. 19, 2005, which claims priority to CH 1750/04 filed Oct 21, 2004, the contents of which are incorporated herein by reference.

The present invention relates to a process for the regioselective N-alkylation of substituted pyrazoles and to the use of trialkyl phosphates or trialkyl phosphonates in the regioselective N-alkylation of substituted pyrazoles.

N-alkylated substituted pyrazoles, for example 3-difluoromethyl-1-methyl-1H-pyrazole-4-carboxylic acid ethyl ester, are valuable intermediates in the preparation of fungicides, as described, for example, in WO 03/074491.

According to WO 95/25099, N-alkylated substituted pyrazoles can be prepared by reacting the corresponding substituted pyrazoles with alkyl halides under basic conditions. The use of alkyl halides in the N-alkylation of substituted pyrazoles is problematic, however, on account of their toxic properties. Furthermore, those compounds are expensive and, in addition, exhibit only a low degree of regioselectivity—in respect of the two nitrogen atoms of the pyrazole ring. For those reasons, such processes are particularly unsuitable for large-scale preparation of N-alkylated substituted pyrazoles.

According to JP-2000-044541, N-alkylated substituted pyrazoles can be prepared by reacting the corresponding substituted pyrazoles with carboxylic acid dialkyl esters, with addition of a base. The use of carboxylic acid dialkyl esters is not desirable, because those compounds are of low reactivity and it is therefore generally necessary to increase the reactivity of the substituted pyrazoles by addition of a base. Furthermore, the regioselectivity of such N-alkylation is generally dependent upon the chemical nature of the substituents on the pyrazole ring, so that N-alkylations using carboxylic acid dialkyl esters in some cases exhibit unsatisfactory regioselectivity.

The aim of the present invention is therefore to provide a novel process for the preparation of N-alkylated substituted pyrazoles that avoids the disadvantages of the known processes mentioned above and makes it possible to prepare those compounds in high yields and good quality in an economically advantageous and easily handled way.

The present invention accordingly relates to a process for the preparation of compounds of formula I

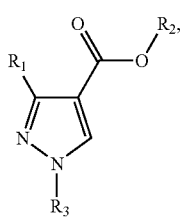

(I)

wherein $R_1$ is $C_1$-$C_4$haloalkyl; $R_2$ is $C_1$-$C_6$alkyl and $R_3$ is methyl or ethyl, by reaction of a compound of formula II

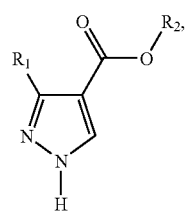

(II)

wherein the substituents are as defined for formula I, with a compound of formula III

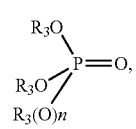

(III)

wherein $R_3$ is as defined for formula I and n is 0 or 1.

The alkyl groups appearing in the above substituent definitions may be straight-chain or branched and are, for example, methyl, ethyl, n-propyl, isopropyl n-butyl, sec-butyl, isobutyl or tert-butyl, preferably methyl or ethyl. Halogen is generally fluorine, chlorine, bromine or iodine, preferably fluorine. $C_1$-$C_4$Haloalkyl groups are derived from the mentioned $C_1$-$C_4$alkyl groups and are preferably difluoromethyl or trifluoromethyl.

The process according to the invention is suitable preferably for the preparation of compounds of formula I wherein $R_1$ is difluoromethyl or trifluoromethyl;

$R_2$ is methyl or ethyl and/or $R_3$ is methyl.

The process according to the invention is especially suitable for the preparation of compounds of formula I wherein $R_1$ is difluoromethyl.

The process according to the invention is very especially suitable for the preparation of compounds of formula I wherein $R_1$ is difluoromethyl; $R_2$ is ethyl and $R_3$ is methyl.

The process according to the invention is also very especially suitable for the preparation of compounds of formula I wherein $R_1$ is trifluoromethyl; $R_2$ is ethyl and $R_3$ is methyl.

In preferred processes, compounds of formula II are reacted with compounds of formula III wherein n is 1.

In especially preferred processes, compounds of formula II are reacted with compounds of formula III wherein n is 1 and $R_3$ is methyl.

The reaction according to the invention is preferably carried out in a temperature range of from 100° C. to 200° C., especially from 150° C. to 200° C.

The reaction according to the invention can be carried out in an anhydrous, inert solvent. Suitable solvents are, for example, xylene, mesitylene, tert-butyl benzene, chlorobenzene, 1,2-dichlorobenzene, Decalin, dibutyl ether, dipentyl ether, diphenyl ether and anisole. The reaction according to the invention is preferably carried out without a solvent.

In the reactions according to the invention, compounds of formula III are used in equimolar amounts or in excess relative to compounds of formula II, preferably in an up to 30-fold excess, especially in an up to 10-fold excess, more especially in a 2-fold to 8-fold excess.

The process according to the invention is very especially suitable for the preparation of compounds of formula I wherein $R_1$ is difluoromethyl, $R_2$ is ethyl and $R_3$ is methyl, by reaction of a compound of formula II wherein $R_1$ is difluoromethyl and $R_2$ is ethyl with a compound of formula III wherein $R_3$ is methyl and n is 1, in a temperature range of from 150° C. to 200° C., without a solvent, the compound of formula III being used in a 2-fold to 8-fold excess relative to the compound of formula II.

The compounds of formula II are known or can be prepared analogously to processes known in the literature. For example, such compounds can be prepared from the 3-oxocarboxylic acid esters on which they are based by means of a two-step synthesis by reaction with trimethyl orthoformate and subsequent reaction with hydrazine. Such reactions are described, for example, in JP-2000-044541. A further synthesis route for the preparation of compounds of formula II is described in JP-2001-322983, wherein, for example, 3-trifluoromethyl-1H-pyrazole-4-carboxylic acid ethyl ester is prepared starting from 3-chloro-4,4,4-trifluoro-2-formyl-2-butenoic acid ethyl ester by reaction with hydrazine.

Compounds of formula III are known as alkylating agents and are commercially available. For example, the N-alkylation of unsubstituted nitrogen-containing heterocycles is described in Journal of the Chemical Society, Perkin Transactions 1, 21, 2506-2508 (1973) and in Bulletin of the Chemical Society of Japan, 50, 1510-1512. There is no mention of such alkylating agents having regioselective properties in the N-alkylation of pyrazoles.

The present invention relates also to the use of compounds of formula III in the regioselective alkylation of compounds of formula II.

The present invention relates also to a process for the regioselective alkylation of compounds of formula II, wherein a compound of formula III is used as alkylating agent.

The present invention is illustrated with the aid of the following Examples:

EXAMPLE P1

Preparation of 3-difluoromethyl-1-methyl-1H-pyrazole-4-carboxylic acid ethyl ester A mixture of 5.7 g of 3-difluoromethyl-1H-pyrazole-4-carboxylic acid ethyl ester (30 mmol) and 25 ml of trimethyl phosphate (214 mmol) is stirred at a temperature of 180° C. for 18 hours. 250 ml of an ice-water mixture are then added. The resulting reaction product is filtered, washed with water and dissolved in 50 ml of ethyl acetate. The organic phase is washed with 50 ml of saturated sodium chloride solution and dried over sodium sulfate and concentrated by evaporation. 3.9 g (64% of theory) of 3-difluoromethyl-1-methyl-1H-pyrazole-4-carboxylic acid ethyl ester are obtained in the form of crystals (m.p. 59-60° C.).

EXAMPLE P2

Preparation of 3-trifluoromethyl-1-methyl-1H-pyrazole-4-carboxylic acid ethyl ester A mixture of 4.16 g of 3-trifluoromethyl-1H-pyrazole-4-carboxylic acid ethyl ester (20 mmol) and 10 ml of trimethyl phosphate (86.4 mmol) is stirred at a temperature of 180° C. for 16 hours. 200 ml of an ice-water mixture are then added. The resulting reaction product is filtered, washed with water and dissolved in 50 ml of ethyl acetate. The organic phase is washed twice with 50 ml of saturated sodium chloride solution each time and dried over sodium sulfate and concentrated by evaporation. 4.0 g (90% of theory) of 3-trifluoromethyl-1-methyl-1H-pyrazole-4-carboxylic acid ethyl ester are obtained in the form of crystals (m.p. 55-57° C.).

EXAMPLE P3

Preparation of 3-trifluoromethyl-1-methyl-1H-pyrazole-4-carboxylic acid ethyl ester A mixture of 2.08 g of 3-trifluoromethyl-1H-pyrazole-4-carboxylic acid ethyl ester (10 mmol) and 2.3 ml of trimethyl phosphate (20 mmol) is stirred at a temperature of 180° C. for 16 hours. 200 ml of an ice-water mixture are then added. The resulting reaction product is filtered, washed with water and dissolved in 50 ml of ethyl acetate. The organic phase is washed twice with 50 ml of saturated sodium chloride solution each time and dried over sodium sulfate and concentrated by evaporation. 1.9 g (86% of theory) of 3-trifluoromethyl-1-methyl-1H-pyrazole-4-carboxylic acid ethyl ester are obtained in the form of crystals (m.p. 55-57° C.).

The following compounds of formula I can be prepared on the basis of the above Examples:

TABLE 1

Compounds of formula I (I)

| Comp. No. | $R_1$ | $R_2$ | $R_3$ |
|---|---|---|---|
| A1 | $CF_2H$ | $CH_2CH_3$ | $CH_3$ |
| A2 | $CF_2H$ | $CH_3$ | $CH_3$ |
| A3 | $CF_2H$ | $CH_3$ | $CH_2CH_3$ |
| A4 | $CF_2H$ | $CH_2CH_3$ | $CH_2CH_3$ |
| A5 | $CF_3$ | $CH_2CH_3$ | $CH_3$ |
| A6 | $CF_3$ | $CH_3$ | $CH_3$ |
| A7 | $CF_3$ | $CH_3$ | $CH_2CH_3$ |
| A8 | $CF_3$ | $CH_2CH_3$ | $CH_2CH_3$ |

The present invention makes it possible for substituted pyrazoles to be alkylated in a controlled manner in a high yield, with a high degree of regioselectivity and at low cost.

A further advantage of the present invention is that substituted pyrazoles can be alkylated without addition of bases.

The starting materials for the process of the present invention are distinguished by ready accessibility and ease of handling and are also inexpensive.

In a preferred embodiment of the invention, the process is carried out without a solvent, such an embodiment constituting an especially inexpensive variant of the process according to the invention.

The invention claimed is:

1. A process for the preparation of a compound of formula I

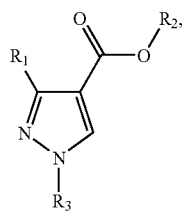
(I)

wherein $R_1$ is $C_1$-$C_4$haloalkyl; $R_2$ is $C_1$-$C_6$alkyl and $R_3$ is methyl or ethyl,
wherein a compound of formula II

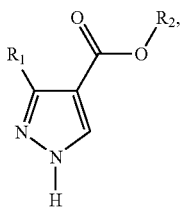
(II)

wherein $R_1$ and $R_2$ are as defined for formula I, is reacted with a compound of formula III

(III)

wherein $R_3$ is as defined for formula I and n is 0 or 1.

2. A process for the regioselective alkylation of a compound of formula II

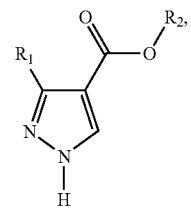
(II)

wherein $R_1$ and $R_2$ are as defined in claim 1, wherein a compound of formula III

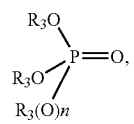
(III)

wherein $R_3$ is as defined in claim 1, is used as alkylating agent.

3. A process according to claim 1, wherein the reaction is carried out without addition of a solvent.

* * * * *